United States Patent
Blumhagen et al.

(10) Patent No.: US 9,753,113 B2
(45) Date of Patent: Sep. 5, 2017

(54) METHOD AND MAGNETIC RESONANCE SYSTEM FOR IMAGING A PARTIAL REGION OF AN EXAMINATION SUBJECT

(75) Inventors: Jan Ole Blumhagen, Erlangen (DE); Matthias Fenchel, Erlangen (DE); Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1224 days.

(21) Appl. No.: 13/606,398

(22) Filed: Sep. 7, 2012

(65) Prior Publication Data
US 2013/0057282 A1 Mar. 7, 2013

(30) Foreign Application Priority Data
Sep. 7, 2011 (DE) ........................ 10 2011 082 266

(51) Int. Cl.
*A61B 5/055* (2006.01)
*G01R 33/565* (2006.01)
*G01R 33/48* (2006.01)

(52) U.S. Cl.
CPC ........ *G01R 33/56563* (2013.01); *A61B 5/055* (2013.01); *G01R 33/56572* (2013.01); *G01R 33/481* (2013.01)

(58) Field of Classification Search
USPC .......................... 324/300–322; 600/407–435
See application file for complete search history.

(56) References Cited

U.S. PATENT DOCUMENTS

| | | | | | |
|---|---|---|---|---|---|
| 4,876,509 A | * | 10/1989 | Perlmutter | ............. | G01R 33/56 324/307 |
| 4,885,542 A | * | 12/1989 | Yao | ................... | G01R 33/56518 324/307 |
| 5,005,578 A | * | 4/1991 | Greer | ................... | G01R 33/565 324/318 |

(Continued)

OTHER PUBLICATIONS

"A Complete Distortion Correction for MR Images: II. Rectification of Static-Field Inhomogeneities by Similarity-Based Profile Mapping," Reinsberg et al, Phys. Med. Biol., vol. 50 (2005), pp. 2651-2661.

(Continued)

*Primary Examiner* — Melissa Koval
*Assistant Examiner* — Tiffany Fetzner
(74) *Attorney, Agent, or Firm* — Schiff Hardin LLP

(57) ABSTRACT

In a method and magnetic resonance (MR) apparatus to image a partial region of an examination subject by means of a multislice measurement, which partial region includes at least two measurement slices, and is located at least in part at the edge of a field of view of the magnetic resonance apparatus, for each voxel to be optimized that is located at the edge of the field of view, a gradient field is configured for each measurement slice of the partial region that is to be measured and is used to acquire magnetic resonance data in the multislice measurement. The gradient field is configured so as to cause a nonlinearity of the gradient field and a $B_0$ field inhomogeneity to cancel at each of the aforementioned voxel to be optimized at the partial region at the edge of the field of view. An image of the partial region of the examination subject is determined from the magnetic resonance data acquired in this manner.

13 Claims, 5 Drawing Sheets

(56) References Cited

U.S. PATENT DOCUMENTS

| | | | | |
|---|---|---|---|---|
| 5,225,779 | A * | 7/1993 | Parker | G01R 33/563 324/306 |
| 5,351,006 | A | 9/1994 | Sumanaweera et al. | |
| 5,498,963 | A | 3/1996 | Schneider et al. | |
| 5,545,995 | A * | 8/1996 | Schneider | G01R 33/56563 324/300 |
| 5,800,354 | A * | 9/1998 | Hofland | G01R 33/56563 324/309 |
| 6,150,815 | A * | 11/2000 | Janzen | B82Y 25/00 324/307 |
| 6,265,873 | B1 * | 7/2001 | Le Roux | G01R 33/5615 324/307 |
| 6,969,991 | B2 * | 11/2005 | Bammer | G01R 33/56518 324/307 |
| 7,511,489 | B2 * | 3/2009 | Fautz | G01R 33/5611 324/307 |
| 8,339,138 | B2 * | 12/2012 | Parker | G01R 33/288 324/318 |
| 2006/0012365 | A1 | 1/2006 | Werthner | |
| 2006/0261810 | A1 * | 11/2006 | Fautz | G01R 33/5611 324/309 |
| 2009/0169083 | A1 | 7/2009 | Li | |
| 2009/0169084 | A1 | 7/2009 | Li et al. | |
| 2010/0102815 | A1 * | 4/2010 | Parker | G01R 33/288 324/309 |
| 2011/0187364 | A1 | 8/2011 | Blumhagen et al. | |
| 2011/0187367 | A1 | 8/2011 | Feiweier et al. | |
| 2012/0056621 | A1 | 3/2012 | Blumhagen et al. | |
| 2012/0187948 | A1 * | 7/2012 | Yamashita | G01R 33/5659 324/318 |
| 2013/0057282 | A1 * | 3/2013 | Blumhagen | A61B 5/055 324/309 |

OTHER PUBLICATIONS

"A Complete Distortion Correction for MR Images: I. Gradient Warp Correction," Doran et al., Phys. Med. Biol., vol. 50 (2005), pp. 1343-1361.

"Impact of Limited MR Field-of-View in Simultaneous PET/MR Acquisition," Delso, et al., Journal of Nuclear Medicine, vol. 49 (2008), p. 162P.

"Analysis of Machine-Dependent and Object-Induced Geometric Distortion in 2DFT MR Imaging," Bakker et al., Magnetic Resonance Imaging, vol. 10, No. 4 (1992), pp. 597-608.

"Multislice 2D Spin-Echo Imaging Using Adapted Readout Gradients for Compensation of B0 Inhomogeneities and Gradient Nonlinearities," Block et al., ESMRMB 2011.

"MR-Based FoV Extension in MR/PET," Blumhagen et al., Deutsche Sektion der ISMRM, Siemens AG (2011).

"MR Geometric Distortion: A Simple Approach to Correcting the Effects of Non-Linear Gradient Fields," Langlois, et al., Journal of Magnetic Resonance Imaging, vol. 9, No. 6 (1999), pp. 821-831.

"MR-Based Field-of-View Extension: Compensation of Field Imperfections," Blumhagen et al, Proc. Intl. Soc. Mag. Reson. Med., vol. 19 (2011), p. 2093.

* cited by examiner

FIG 3
Simulated Distortion in Slices without Inventive Correction
a)
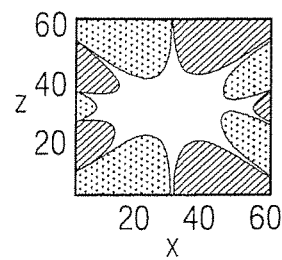
b)
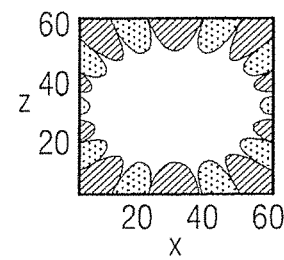
c)
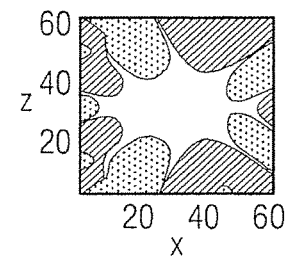
d)
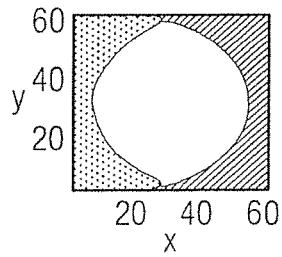
e)
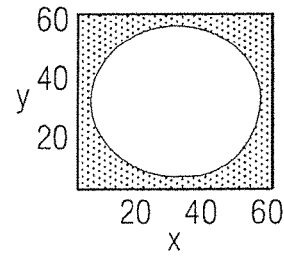
f)
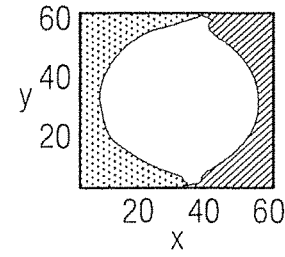

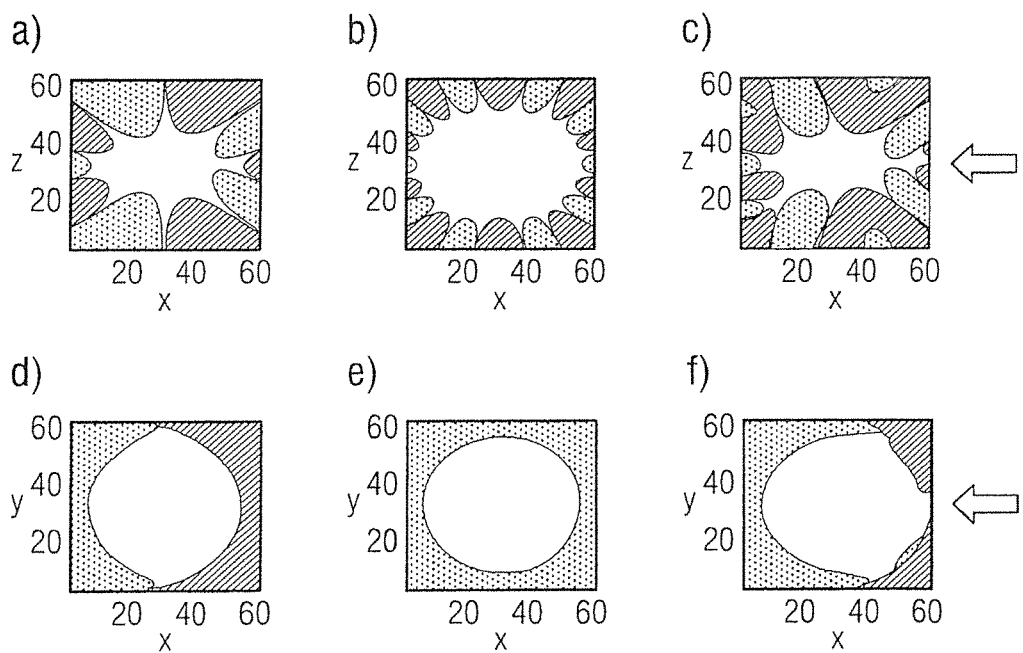

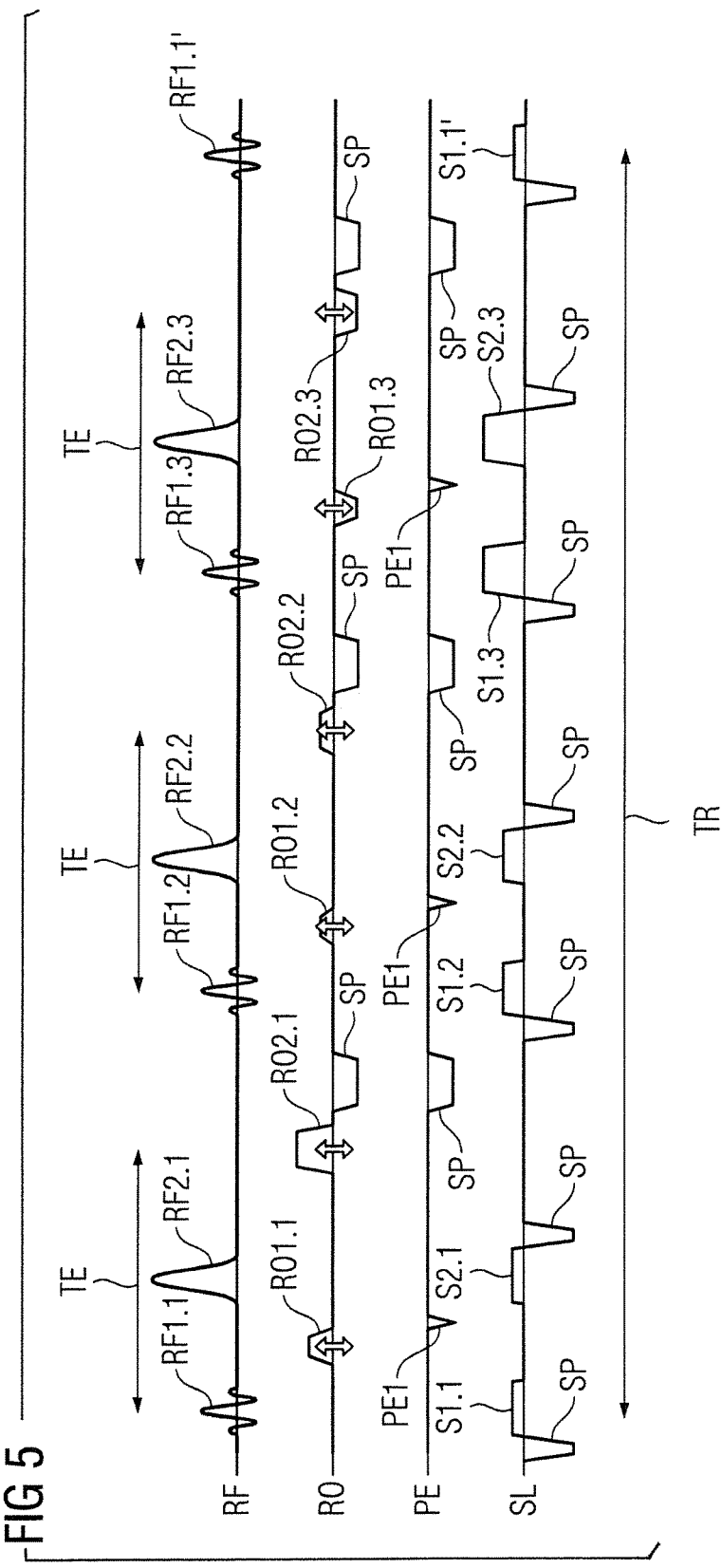

METHOD AND MAGNETIC RESONANCE SYSTEM FOR IMAGING A PARTIAL REGION OF AN EXAMINATION SUBJECT

BACKGROUND OF THE INVENTION

Field of the Invention

The present invention concerns a method for imaging a partial region of an examination subject in a magnetic resonance system, and a magnetic resonance system designed to implement such a method.

Description of the Prior Art

In a magnetic resonance system, the volume in which magnetic resonance data are acquired is limited in all three spatial directions due to physical and technical conditions (for example a limited magnetic field homogeneity and the nonlinearity of the gradient field). The acquisition volume—known as a "field of view" (FoV)—is therefore limited to a volume in which the aforementioned physical features lie within a predetermined tolerance range, and thus in which an image of the subject to be examined that is true to scale is possible with typical measurement sequences. The FoV is limited in the x-direction and y-direction, i.e. perpendicular to a longitudinal axis of a tunnel of the magnetic resonance system, but less significantly than the volume limited by the annular tunnel of the magnetic resonance system. In typical magnetic resonance systems a diameter of the annular tunnel amounts to approximately 60 cm, in contrast to which the diameter of the FoV that is typically used (in which the aforementioned physical features lie within the tolerance region) amounts to approximately 50 cm.

In many applications of magnetic resonance systems, this inadequacy (that no imaging of the measurement subject that is true to scale is possible in the boundary region of the tunnel of the magnetic resonance system) does not represent any great problem since, in basic magnetic resonance exposures, the region of the subject to be examined typically can be arranged in the magnetic resonance system such that this region is not located at the edge of the tunnel, but is optimally in the center of the tunnel (in what is known as the isocenter of the magnetic resonance system). Particularly in hybrid systems (for example a hybrid system having a magnetic resonance tomographic scanner and a positron emission tomographic scanner, known as an MR-PET hybrid system), it is frequently of great importance to also determine structures of the examination subject with as optimal a precision as possible in the boundary region. For example, the human attenuation correction is of decisive importance in an MR-PET hybrid system. The intensity attenuation of the photons emitted after an interaction of positrons and electrons on their way through absorbing tissue to the detector is determined with the human attenuation correction, and the received signal of the PET is corrected with precisely this attenuation. For this purpose, a magnetic resonance exposure is acquired that depicts the complete anatomy of the subject to be examined in the direction of the high-energy photons emitted by the positron emission scanner. It is also desired to acquire anatomy of the subject to be examined as precisely as possible in the boundary region of the tunnel of the hybrid system. When the subject to be examined is a patient, structures that are located in these regions are primarily the arms, which can be arranged near the inner tunnel wall of the hybrid system, in the boundary region.

In other applications of magnetic resonance systems—for example simply an examination of a particularly large (for example adipose) patient or stereotactic biopsies or other procedures to be executed during image monitoring—it can also be desirable to be able to expand the field of view to the boundary regions of the tunnel of the magnetic resonance system.

A method to determine an attitude of a partial region of an examination subject in a magnetic resonance system is provided in German Patent Application DE 10 2010 006 431.9. The partial region of the examination subject is arranged at the edge of the field of view of the magnetic resonance system. In this method, at least one slice position for a magnetic resonance image is determined automatically for which the $B_0$ field at the edge of the magnetic resonance image satisfies a predetermined homogeneity criterion. Furthermore, a magnetic resonance image is acquired in this determined slice position that includes the partial region at the edge of the field of view. The attitude of the partial region of the examination subject is determined by the attitude of the partial region in the acquired magnetic resonance image.

Furthermore, in an article by Delso et al., a method has been proposed in order to compensate for the missing information in the magnetic resonance image (which information is missing due to the limitation of the field of view) by segmentation of the body contours using uncorrected PET data (G. Delso et al., Impact of limited MR field-of-view in simultaneous PET/MR acquisition, J. Nucl. Med. Meeting Abstracts, 2008; 49, 162P).

Since the field of view of a magnetic resonance system is limited to a volume in which the magnetic field inhomogeneity and the nonlinearity of the gradient field lie within specified regions, in the prior art various correction algorithms have been proposed in order to extend the field of view. For example, a gradient distortion correction is proposed in Langlois S. et al., MRI Geometric Distortion: a simple approach to correcting the effects of non-linear gradient fields, J. Magn. Reson. Imaging 1999, 9(6), 821-31, and in Doran S J et al., A complete distortion correction for MR images: I. Gradient warp correction, Phys. Med. Biol. 2005 Apr. 7, 50(7), 1343-61. Furthermore, a corresponding $B_0$ field correction is proposed in Reinsberg S A, et al., A complete distortion correction for MR images: II. Rectification of static-field inhomogeneities by similarity-based profile mapping, Phys. Med. Biol., 2005 Jun. 7, 50(11), 2651-61.

SUMMARY OF THE INVENTION

Extending (enlarging the, a field of view (for example as would be particularly advantageous for an application in a whole-body MR-PET) is not known in the prior art. Therefore, it is an object of the present invention to provide a suitable, true-to-scale imaging of structures of a subject to be examined in a region across multiple measurement slices outside of the typical field of view, for example in a boundary region of the annular tunnel of the magnetic resonance system.

Given severe distortions in these boundary regions in which the $B_0$ field inhomogeneities and the gradient field have nonlinearities, a subsequent compensation of the distortion in the magnetic resonance exposure is frequently not possible since the distorted regions overlap in the magnetic resonance exposure. Therefore, it is also an object of the present invention to already avoid severe distortions at the point in time of the acquisition of magnetic resonance data.

According to the present invention, a method is provided for imaging a partial region of an examination subject that has at least two measurement slices in a magnetic resonance system. The partial region is at least partially arranged at the edge of a field of view of the magnetic resonance system.

In the method, a partial region to be measured is initially selected by a user. For example, a number of measurement slices to be measured and their positions, as well as the voxel size to be used in the measurement slice measurement (voxels: volumes of the examination subject which indicates the smallest resolution of the measurement, sometimes also designated as a pixel, measurement location or measurement point) can thereby be selected. Gradients of a respective gradient field for at least one voxel of the partial region that is to be optimized (this at least one voxel being located at the edge of the field of view) are then generated for each measurement slice of the partial region, which gradients have been defined such that a distortion caused by a nonlinearity of the gradient field and a distortion caused by a $B_0$ field inhomogeneity cancel out at each of the aforementioned voxels at the edge of the field of view that are to be optimized. Using the generated gradients for each measurement slice, magnetic resonance data of the partial region are acquired by means of a multislice measurement and an image of the partial region of the examination subject is determined from the magnetic resonance data.

In a multislice measurement, the fact is utilized that the echo time TE is markedly shorter than the recovery period of a first excited slice which establishes the repetition time TR of the sequence. Additional measurement slices therefore can be excited and measured in the time interval between an excitation and the recovery of the spins that are thereby excited. Multiple measurement slices thus can be excited and measured (data acquired therefrom) during a repetition time TR, which entails a not insignificant time savings. The measurement slices that are thus measured are interleaved.

According to the invention, a gradient that generates a gradient field is used for each of these measurement slices, which gradient has been defined such that a distortion caused by a nonlinearity of the gradient field and a distortion caused by a $B_0$ field inhomogeneity cancel out at the respective voxel to be optimized in each measurement slice. Distortions are thus also reduced in the boundary region of the field of view of the magnetic resonance system. The gradient field can be, for example, a readout gradient field or a slice selection gradient field.

Since the nonlinearity of the gradient field depends on the gradient field strength and the $B_0$ field inhomogeneities are independent of the gradient field strength, the gradient field can be adjusted and generated for each voxel in the field of view such that the nonlinearity of the gradient field and the $B_0$ field inhomogeneity cancel out at this voxel. A distortion for this voxel can thereby be avoided.

In this context, "distortion" means that a signal value of a predetermined location (x, y, z) of the examination subject (for example at a predetermined location at the edge of the field of view) appears at a different location $(x_1, y_1, z_1)$ in the image of the examination subject that is determined from the acquired magnetic resonance data. The coordinates (x, y, z) are also designated as the actual position, the coordinates $(x_1, y_1, z_1)$ are also designated as the distorted position. In particular, distortions can occur in the boundary regions of the field of view which cannot be compensated by subsequent distortion correction of the image of the examination subject, since multiple adjacent actual positions can be mapped to one distorted position or multiple distorted positions of the densely situated distorted positions. Because the nonlinearity of the gradient field and the $B_0$ field inhomogeneity mutually cancel at a predetermined location or region by the generation of a suitable gradient field, no distortions (or only slight distortions) occur for this region such that an evaluable image of the examination subject can be determined in this region.

According to one embodiment, a relative gradient error is determined, at least at each desired voxel, at the edge of the field of view in order to generate the gradient field. Furthermore, the $B_0$ field inhomogeneity is determined for at least each desired voxel. The relative gradient errors and the $B_0$ field inhomogeneity can be determined in advance, for example by calibration of the magnetic resonance system. Depending on the relative gradient error and the $B_0$ field inhomogeneity, the gradient of the gradient field is then determined and generated accordingly upon acquisition of the magnetic resonance data.

The gradient G of the gradient field can be determined according to the following equation $$G=-dB_0(x,y,z)/c(x,y,z), \qquad (1)$$

wherein $dB_0$ is the $B_0$ field inhomogeneity at the predetermined location (x, y, z) at the edge of the field of view and c is the relative gradient error at the predetermined location (x, y, z). The equation applies analogously to voxels ($\Delta x$, $\Delta y$, $\Delta z$) instead of locations (x, y, z).

If the magnetic resonance system has been measured once—meaning that the relative gradient errors and the $B_0$ field inhomogeneity for specific voxels or regions (for example regions in which the arms of the patient presumably lie) have been determined—gradients of the gradient field can thus be determined and generated in a simple manner in order to be able to reliably determine an image of the examination subject at the predetermined voxel, i.e. without distortion.

In principle, to generate the gradient field the $B_0$ field inhomogeneity at selected voxels at the edge of the field of view can also be determined, and a gradient coil can be designed to generate the gradient field such that a nonlinearity of the gradient field and the $B_0$ field inhomogeneity cancel each other at the selected voxel. For example, since typically only a few regions at the edge of the field of view of the magnetic resonance system (for example regions in which the arms of the patient are presumably located) must be acquired without distortion for a PET attenuation correction, a gradient coil can be optimized to the effect that the inhomogeneity of the gradient coil essentially cancels out the $B_0$ field inhomogeneity in this regions given a predetermined gradient field. A distortion-free imaging of the examination subject in these predetermined regions thus can be achieved.

In principle, to generate the gradient field it is also possible to determine the nonlinearity of the gradient field at the selected location at the edge of the field of view and to vary the $B_0$ field such that the nonlinearity of the gradient field and the $B_0$ field inhomogeneity cancel out at the selected voxel. The variation of the $B_0$ field can be adjusted, for example, by suitable arrangement of shim plates. A slight distortion, or even no distortion at all, can be achieved in this manner for at least a few predetermined regions (for example regions in which the arms of the patients are expected to be situated).

The method can in particular be used in a magnetic resonance system with a tunnel-shaped opening to accommodate the examination subject. The edge of the field of view of such a magnetic resonance system a sheath-like region along an inner surface of the tunnel-shaped opening. The sheath region can have a thickness of approximately 5 cm, for example. As noted above, the partial region of the examination subject that is to be imaged can be an anatomical structure of the patient, in particular (for example) an arm of the patient that is arranged at the edge of the field of view of the magnetic resonance system. The magnetic resonance data are advantageously acquired in a transverse plane relative to the examination subject.

Due to the low distortion, the determined image is of high quality even in the boundary region of the field of view, which is why examination regions of adipose patients (for example) that cannot be arranged closer to the center of the tunnel of the magnetic resonance system can also be examined by means of MR. Furthermore, the determined image can be used, for example, in the positioning of stereotactic devices or implementation of stereotactic procedures, and/or the attitude of the partial region can be reliably determined in the determined image of the examination subject.

According to a further embodiment, an attenuation correction for a positron emission tomography (PET) scanner is determined depending on an attitude of the partial region of the examination subject. Due to the low distortion, the attitude of the partial region (an arm, for example) can be determined reliably from the image of the examination subject. In positron emission tomography, consideration of attenuation of the received radiation (photons) by the structure or anatomy of the examination subject in the beam direction is of decisive importance. Because the attitude of the partial region of the examination subject can be determined even at the edge of the field of view of the magnetic resonance system, a complete determination of the attitude and structure of the examination subject or patient in the magnetic resonance system is possible, and thus a precise attenuation correction for positron emission tomography is achievable. Since the attenuation correction is in this case based solely on information from the magnetic resonance imaging, positron emission tomography can also be implemented with less strongly enriched PET tracers (rubidium, for example).

The determination of the attitude of the partial region of the examination subject at the edge of the field of view of the magnetic resonance system likewise provides assistance in a radiotherapy planning.

According to the present invention, a magnetic resonance system is furthermore provided that has a control device to control a scanner (data acquisition unit) with a magnet to generate a $B_0$ field, a receiver device to receive signals acquired by the scanner; and an evaluation device to evaluate the signals and generate magnetic resonance images. The magnetic resonance system is able to generate (configure) gradients of a respective gradient field for a respective voxel of a selected partial region having at least two measurement slices (which voxel is to be optimized and is arranged at the edge of the field of view of the magnetic resonance system), which partial region is located at least partially at the edge of the field of view. The gradients are determined such that a nonlinearity of the gradient field and a $B_0$ field inhomogeneity cancel at each of the cited voxels at the edge of the field of view. For example, a partial region of an examination subject that is to be imaged with the aid of the magnetic resonance system can be located at the edge of the field of view. The magnetic resonance system is also designed so as to acquire magnetic resonance data of the partial region with the use of a multislice measurement using the gradients configured for each measurement slice. The magnetic resonance system then determines an image of the partial region of the examination subject from the acquired magnetic resonance data.

The magnetic resonance system can also have a positron emission tomography scanner (data acquisition unit) and can automatically determine an attenuation correction for a positron emission tomography data acquisition depending on the determined image of the examination subject in the magnetic resonance system.

Since, the magnetic resonance system is designed to implement the previously described method and its embodiments, it therefore exhibits the advantages described in the preceding.

The present invention furthermore encompasses a non-transitory, electronically readable data storage medium (for example a CD or DVD) on which are stored electronically readable control information/commands (in particular software). All embodiments according to the invention of the previously described method can be executed with the magnetic resonance system when this control information is read from the data medium by n a control unit of the magnetic resonance system.

BRIEF DESCRIPTION OF THE DRAWINGS

FIG. 3 shows an example of a simulated distortion with a readout direction in the x-direction, with a readout gradient that was not generated according to the present invention.

FIG. 4 shows an example of a simulated distortion with a readout direction in the x-direction, with a readout gradient generated according to the present invention.

FIG. 5 schematically illustrates a pulse sequence that can be used to implement the method according to the invention.

DESCRIPTION OF THE PREFERRED EMBODIMENTS

Figure 1:
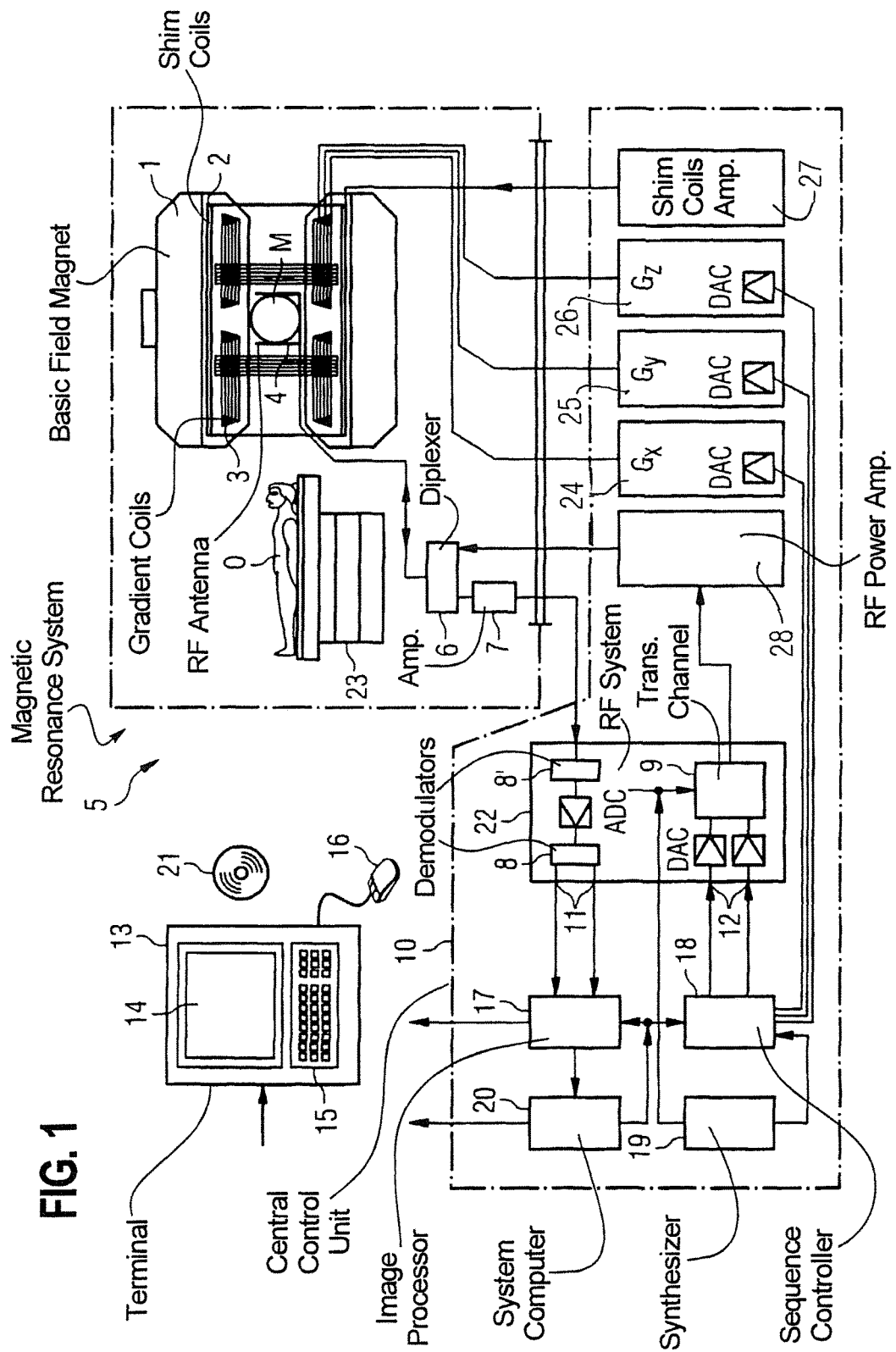
FIG. 1 schematically shows a magnetic resonance system according to an embodiment of the present invention.

FIG. 1 is a schematic representation of a magnetic resonance system 5 (of a magnetic resonance imaging or magnetic resonance tomography apparatus). A basic magnet 1 generates a temporally constant, strong magnetic field for polarization or alignment of the nuclear spins in an examination region of an examination subject U (for example a part of a human body that is to be examined) that lies on a table 23 and is moved into the magnetic resonance system 5. The high homogeneity of the basic magnetic field that is required for the magnetic resonance measurement (data acquisition) is defined in a typically spherical measurement volume M in which the parts of the human body that are to be examined are introduced. Shim plates made of ferromagnetic material (which may be selectively adaptable) are mounted at a suitable location to support the homogeneity requirements, and in particular to eliminate temporally invariable influences. Temporally variable influences are eliminated by shim coils 2 and a suitable shim coil amplifier 27 for the shim coils 2.

A cylindrical gradient coil system 2 composed of three sub-windings is inserted into the basic magnet 1. The sub-windings are respectively supplied with current by respective amplifiers 24-26 to generate a linear gradient field in the respective direction of a Cartesian coordinate system. The first sub-winding of the gradient field system 3 generates a gradient $G_x$ in the x-direction; the second sub-winding generates a gradient $G_y$ in the y-direction; and the third sub-winding generates a gradient $G_z$ in the z-direction. Each of the amplifiers 24-26 has a digital/analog converter (DAC)

controlled by a sequence controller 18 for accurate timed generation of gradient pulses.

Located within the gradient field system 3 is a radio-frequency antenna 4 that translates the radio-frequency pulses emitted by a radio-frequency power amplifier 28 into an alternating magnetic field to excite the nuclei and align the nuclear spins of the subject to be examined, or of the region of the subject that is to be examined. The radio-frequency antenna 4 has one or more RF transmission coils and multiple RF reception coils in the form of a (for example) annular, linear or matrix-like arrangement of coils. The alternating field emanating from the precessing nuclear spins—i.e. normally the nuclear spin echo signals produced by a pulse sequence composed of one or more radio-frequency pulses and one or more gradient pulses—is also transduced by the RF reception coils of the radio-frequency antenna 4 into a voltage (measurement signal), which is supplied via an amplifier 7 to a radio-frequency acquisition channel 8, 8' of a radio-frequency system 22. The radio-frequency system 22 furthermore has a transmission channel 9 in which the radio-frequency pulses are generated for the excitation of the nuclear magnetic resonance signals. The respective radio-frequency pulses are thereby digitally represented in the sequence controller 18 as a series of complex numbers based on a pulse sequence provided by the system computer 20. This number series is supplied as a real part and imaginary part via respective inputs 12 to a digital/analog converter (DAC) in the radio-frequency system 22, and from this to the transmission channel 9. In the transmission channel 9 the pulse sequences are modulated on a radio-frequency carrier signal whose basic frequency corresponds to the resonance frequency of the nuclear spins in the measurement volume. The modulated pulse sequences are supplied via an amplifier 28 to the RF transmission coil of the radio-frequency antenna 4.

The switching from transmission mode to reception mode takes place via a transmission/reception diplexer 6. The RF transmission coil of the radio-frequency antenna 4 radiates the radio-frequency pulses for the excitation of the nuclear spins into the measurement volume M and scans resulting echo signals via the RF reception coils. The correspondingly obtained nuclear magnetic resonances signals are phase-sensitively demodulated to an intermediate frequency in a first demodulator 8' of the acquisition channel of the radio-frequency system 22 and are digitized in the analog/digital converter (ADC). This signal is further demodulated to a frequency of zero. The demodulation to a frequency of zero and the division into real part and imaginary part occurs after the digitization in the digital domain in a second demodulator 8 which emits the demodulated data via outputs 11 to an image computer 17. An MR image is reconstructed by the image computer 17 from the measurement data acquired in such a manner. The administration of the measurement data, the image data and the control programs takes place via the system computer 20 at which additional information (for example data about $B_0$ field inhomogeneities and gradient nonlinearities or other data usable for specific measurements, for example gradients determined according to the invention for a defined set of voxels of the boundary region of the field of view) can be stored so as to be retrievable. The sequence controller 18 monitors the generation of the respective desired pulse sequences and the corresponding scanning of k-space based on a specification with control programs. In particular, the sequence controller 18 controls the accurate timed switching of the gradients, the emission of the radio-frequency pulses with defined phase amplitude and the reception of the nuclear magnetic resonance signals.

The time base for the radio-frequency system 22 and the sequence controller 18 is provided by a synthesizer 19. The selection of corresponding control programs to generate an MR image (which control programs are stored on a DVD 21, for example) as well as other inputs on the part of the user and the presentation of the generated MR image take place via a terminal 13, which has input means to enable an input (for example a keyboard 15 and/or a mouse 16) and display means (for example a monitor 14) to enable a display. For example, via the input means a user can also select a partial region 51 to be examined that includes multiple measurement slices, for example two measurement slices 51.1 and 51.2. Furthermore, a voxel to be optimized can be selected if necessary at each measurement slice of the partial region.

The measurement volume M—which is also called field of view (FoV)—is limited on the hardware side by the $B_0$ field homogeneity and the linearity of the gradient field. Measurements outside of this measurement volume—thus in regions in which the $B_0$ field inhomogeneities and the gradient field have nonlinearities—lead to strong distortions, meaning that regions of the examination subject which are arranged outside of the measurement volume M do not appear in the magnetic resonance image at the point at which they are actually located, but rather at a position offset from this. For a magnetic resonance scanner with a tube diameter of 60 cm, for example, the measurement volume M typically has a diameter of 50 cm. In magnetic resonance scanners with a larger or smaller tube diameter, the measurement volume accordingly has a larger or smaller size. This means that the distortion occurs in a region from approximately 5 cm to approximately 10 cm in a boundary region along the inner circumference of the tomograph. The arms of a patient may be located in this region, for example. Due to the distortion, the position of the arms or the position of another examination region of the patient that is located in the boundary region of the field of view can be incorrectly rendered in the magnetic resonance exposure. Therefore the magnetic resonance exposures in this region are not usable for a human attenuation correction in MR-PET hybrid systems, for example.

The distortions that occur in this boundary region depend on the field deviation dBg or, respectively, $dBg_0$ from the nominal value and on the gradient field strength G. This connection is known from Bakker C J, et al., Analysis of machine-dependent and object-induced geometric distortion in 2DFT MR imaging, Magn Reson Imaging, 1992, 10(4): 597-608. The following equations describe examples of a 2-dimensional magnetic resonance data acquisition with slice selection in the z-direction, phase coding in the y-direction and frequency coding in the x-direction. The phase coding direction, the frequency coding direction and the slice selection direction are freely selectable and merely adapt the axis length to the equations.

$$z_1 = z + dB_{gz}(x,y,z)/G_z + dB_0(x,y,z)/G_z \quad (2)$$

$$x_1 = x + dB_{gx}(x,y,z)/G_x + dB_0(x,y,z)/G_x \quad (3)$$

$$y_1 = y + dB_{gy}(x,y,y[\text{sic}])/G_y \quad (4)$$

The coordinates (x,y,z) designate the actual positions, and the coordinates $(x_1,y_1,z_1)$ designate the distorted positions.

FIG. 3 shows a simulation of the distortion in the x-direction given a switched readout gradient in the x-direction of $G_x=10$ mT/m in a coronal slice view due to the gradient field (image a), the $B_0$ field (image b) and the superposition of the two fields (image c), as well as in a transverse slice view due to the gradient field (image d) of the $B_0$ field (image e) and the superposition of the two fields (FIG. 3f). In FIG. 3 the distortions are designated with different fill patterns. Regions in which essentially no distortion occurs contain no pattern; regions with positive distortion are stippled and regions with negative distortion are hatched. The distortion can have different values within the respective regions. In the regions without pattern—i.e. in the regions that essentially have no distortion—the distortion is less than +/−1 mm, for example. In the stippled regions, the distortion amounts to +1 mm to +20 mm or even beyond, for example. In the hatched regions, the distortion amounts to −1 to −20 mm or beyond, for example. The distortion generally proceeds continuously, meaning that the distortion in the regions grows outward from the isocenter, wherein in FIG. 3 the isocenter lies at x=30, y=30 and z=30, for example.

Since the nonlinearity dBg of the gradient field scales with the gradient field strength, the distortion for a specific region or location can be specifically reduced or compensated, as described below, starting from $$dB_{gx} = c(x,y,z) \cdot G_x \quad (5)$$

wherein $c(x, y, z)$ designates the relative gradient errors at the point x, y, z and $G_x$ represents the gradient field strength. The $B_0$ field inhomogeneities, however, are constant, independent of the field strength. The term $dB_{gx}/G_x$ is thus constant and independent of the gradient field strength. However, the term $dB_0/G_x$ is variable with the gradient field strength. According to the present invention, the magnetic fields are therefore superimposed such that the nonlinearity of the gradient field and the $B_0$ field inhomogeneity destructively superimpose at a predetermined location or a predetermined region. For example, this is described in the following for a readout gradient in the x-direction with a slice selection in the z-direction. The required destructive superposition of the magnetic fields is achieved when an optimal gradient strength $G_{x\_opt}$ exists for which the distortion is zero at a predetermined location or within the predetermined region. Given a distortion of zero in the x-direction, $$x_1 = x$$

From this, it follows that:

$$G_{x\_opt}(x,y,z) = -dB_0(x,y,z)/c(x,y,z) \quad (6)$$

If the gradient field strength $G_x$ is selected as described in Equation (6), a markedly enlarged field of view results for the predetermined position or the predetermined region, meaning that the distortion significantly decreases in this region.

FIG. 4 shows an example of a simulated distortion given a readout gradient in the x-direction with a readout gradient $G_x$=4.3 mT/m that was determined according to Equation (6). Comparable to FIG. 3, image a in FIG. 4 shows the distortion in a coronal slice due to the gradient field, image b shows the distortion in the coronal slice due to the $B_0$ field and image c shows the distortion in the x-direction given superposition of the two fields. Image d in FIG. 4 accordingly shows the distortion in the x-direction in a transverse slice due to the gradient field, image e shows the distortion in the transverse slice due to the $B_0$ field and image f shows the distortion due to the superposition of the two fields in the transverse slice. The nonlinearity of the gradient field precisely superimposes with the inhomogeneity of the $B_0$ field at the position that is respectively marked in images c and f in FIG. 4, such that the distortion there goes to zero.

FIG. 5 shows a portion of a pulse sequence of a multislice measurement that can be used in connection with the present invention. The shown portion of the pulse sequence is based on a 2D spin echo multislice measurement in which an excitation pulse RF1.1 is radiated and a slice selection gradient S1.1 is simultaneously switched. After the excitation pulse RF1.1, a phase coding gradient PE1 is switched for spatial coding and a dephasing gradient R01.1 is switched in the readout direction. A refocusing pulse RF2.1 is subsequently radiated, and a slice selection gradient S2.1 is simultaneously switched again which encodes the same slice as S1.1.

After the refocusing pulse RF2.1, at the echo point in time an echo signal (not shown) arises which is acquired for additional spatial coding while switching a readout gradient R02.1 and is stored by the magnetic resonance system. The time interval between the excitation pulse RF1.1 and the refocusing pulse RF2.1 corresponds to the time interval between the refocusing pulse RF2.1 and the echo point in time. The time interval between the excitation pulse RF1.1 and the echo point in time is also designated as an echo time TE.

Given a multislice measurement, the repetition period of the first excited slice S1.1, S2.1 is utilized in order to measure additional measurement slices according to [sic] partial region to be measured. In the shown example, two additional measurement slices S1.2, S2.2, S1.3, S2.3 are furthermore excited and measured in the repetition period which corresponds to the repetition time TR. Depending on TR and TE, markedly more measurement slices can actually also be measured in an interleaved manner in a repetition time TR.

In general, as shown, a respective additional exposure pulse RF1.2, RF1.3 is radiated, and at the same time a corresponding slice selection gradient S1.2 or S1.3 is switched, wherein the slice selection gradients S1.1, S1.2 and S1.3 respectively encode a different measurement slice. In the additional measurement slices, after the respective excitation pulse RF1.2 or RF1.3 phase coding gradient PE1 is switched as in the first measurement slice S1.1, S2.1 and adapted dephasing gradients R01.2, R01.3 are switched in the readout direction for spatial coding thereof. The refocusing pulses RF2.2, RF2.3 are again radiated with simultaneous switching of slice selection gradients S2.2, S2.3, wherein S1.2 and S2.2 as well as S1.3 and S2.3 respectively encode the same measurement slice again. An echo signal respectively arises again after the echo time TE after the excitation pulses RF1.2, RF1.3, which echo signal is acquired for additional spatial coding while switching a readout gradient R02.2 or, respectively, R02.3 with an acquisition antenna and is stored by the magnetic resonance system.

As is schematically represented by double arrows, the readout gradients R01.1, R02.1, R02.2, R01.3, R02.3 are respectively, automatically adapted according to the criteria described above in terms of strength and polarity to the associated respective measurement slice S1.1, S2.1 or S1.2, S2.2, or S1.3, S2.3, or more precisely to the voxel of the partial region that is to be measured, which voxel is to be optimized and is comprised in the respective measurement slice.

Furthermore, spoiler gradients SP can be switched in the slice selection direction SL and/or in the readout direction RO and/or in the phase coding direction PE to suppress unwanted signals.

After the repetition time TR after the first excitation pulse RF1.1, the shown sequence repeats again in principle. A new excitation pulse RF1.1' is radiated while switching the slice selection gradient S1.1', wherein S1.1' codes the same measurement slice as the first slice selection gradient S1.1. In the repetition time following this excitation pulse RF1.1', the shown sequence is repeated with measurement slices corresponding to the respective measurement slices measured in the first repetition time TR, and with readout gradients (no longer shown) respectively corresponding to the readout gradients R01.1, R02.1, R01.2, R02.2, R01.3, R02.3 in the first repetition time TR given measurement of the same measurement slice, but said repetition takes place with different phase coding gradients PE according to the desired measurement volume.

Multiple measurement slices are thus excited and measured during a repetition time TR. For each of these measurement slices, a gradient field has been defined such that a distortion caused by a nonlinearity of the gradient field and a distortion caused by a $B_0$ field inhomogeneity cancel at the voxels that are to be optimized in each measurement slice.

Figure 2:
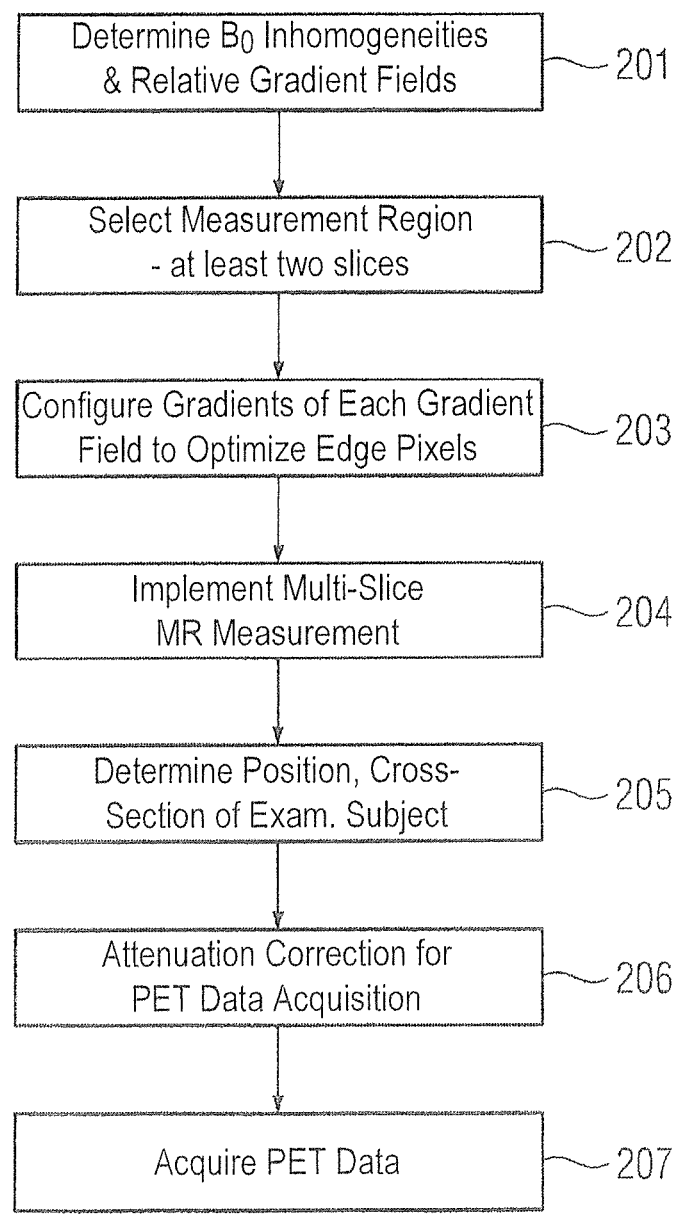
FIG. 2 is a flowchart for an embodiment of a method according to the invention.

The previously described methods can advantageously be used for human attenuation correction of an MR-PET hybrid system, for example. The method described in connection with FIG. 2 leads to an enlarged magnetic resonance-based field of view that is measurable in a shorter amount of time, and thus supports (for example) the MR-PET attenuation correction even with magnetic resonance data outside the typically specified field of view of the magnetic resonance system.

For this purpose, as is shown in Step 201, the $B_0$ field and the gradient field of the magnetic resonance system are initially determined in order to determine the $B_0$ field inhomogeneities and the relative gradient fields of the magnetic resonance system. It is already sufficient if this is implemented once upon installation of the magnetic resonance system, insofar as the $B_0$ field and the gradient coils are not modified, or after each variation of $B_0$ field and/or gradient coils. The determined values of the $B_0$ field inhomogeneities and the relative gradient fields of the magnetic resonance system are stored in the system computer of the magnetic resonance system, for example.

As is shown in Step 202, before the start of the multislice measurement a partial region to be measured—which partial region includes at least two measurement slices—is selected, for example by a user. A voxel to be optimized, which voxel is arranged in the boundary region of the field of view and included by the partial region, is determined per measurement slice of this partial region. The determination of the voxel to be optimized can take place automatically via predetermined selection criteria, for example in that that voxel which is arranged furthest from the center of the field of view or which is arranged at a location with particularly high $B_0$ field inhomogeneity and/or gradient nonlinearity is determined per measurement slice as a voxel to be optimized. The voxel to be optimized can also possibly be selected manually by the user.

The selected partial region is located at least partially at the edge of the field of view of the magnetic resonance system, meaning that the selected partial region includes voxels which are arranged in the boundary region of the field of view. For example, the user thereby indicates a desired number of measurement slices, the desired slice thickness δz and their slice position, as well as a desired voxel size (spatial resolution ($\Delta x, \Delta y, \Delta z$)) and the positions of the voxels that are to be optimized.

In Step 203, gradients of a respective gradient field are then configured (designed) for each voxel of the partial region that is to be optimized at the edge of the field of view, which voxels have been determined such that a distortion caused by a nonlinearity of the gradient field and a distortion caused by a $B_0$ field inhomogeneity cancel at each of the cited voxels at the edge of the field of view. Since the slice selection gradients and the readout gradients are switched identically in each repetition time TR for the multislice measurement, an array of each optimal gradient strength and gradient polarity of the readout gradient is thus determined and configured for each voxel to be optimized of each selected measurement slice of the partial region. The nonlinearity of the gradient field and the $B_0$ field inhomogeneity are thereby destructively superimposed at each cited optimized voxel. The distortions are likewise also reduced in this way in the regions adjacent to the cited optimized voxels (same gradient switching as given optimized voxels, except for a different phase coding gradient PE), albeit not to the same extent as given the optimized voxels.

The configured (designed) gradients have been determined as described above depending on the stored relative gradient error and the $B_0$ field inhomogeneity. This can already have taken place before the start of the measurement, for example in that the described gradients have been determined and stored for all reasonably appearing voxels at the edge of the field of voxels and have been provided to the system computer. However, it is also conceivable that the gradients are only determined after selection of the partial region to be measured. The latter is in particular reasonable if only rarely required voxels of the boundary region of the field of view are included in the selected partial region and should be optimized.

In Step 204, a multislice measurement which measures the selected partial region is implemented using the calculated gradient fields.

A position and a cross section of the examination subject can be determined in Step 205 from each transverse magnetic resonance image corresponding to a measurement slice. The steps 201-205 can if necessary be implemented successively for various desired partial regions in order to determine a complete arrangement of the examination subject in the magnetic resonance with optimal precision but— by the multislice measurement—with relatively small time cost in comparison to a plurality of individual measurements. However, the magnetic resonance images acquired by means of the multislice measurement—which thus deliver low-distortion images of the examination subject even in the boundary region of the field of view of the magnetic resonance system—are also usable for other purposes (see above).

In Step 206, an attenuation correction for the PET acquisition can be determined from the determined positions and the determined cross sections of the examination subject. Finally, PET data can be acquired in Step 207, and from this a PET exposure can be calculated using the attenuation correction.

For each measurement slice, the multislice measurement thus possesses gradient fields that are calculated and used automatically and are adapted in terms of both strength and polarity. It is therefore possible to simultaneously compensate for existing $B_0$ field inhomogeneities due to the gradient nonlinearities in a measurement and in multiple measurement slices, and thus to expand the measurable field of view in the positive and negative x-direction beyond the normally specified field of view, whereupon up to the entire inner tunnel space can be measured by means of MR.

Although exemplary embodiments have been described in the preceding specification, various modifications can be realized in additional embodiments. For example, a 3-dimensional magnetic resonance data acquisition is also possible with the method of the present invention that is described in the preceding. Since in this case the slice selection is replaced with an additional phase coding, the $B_0$ term in Equations (2) through (4) in the slice selection direction would be omitted. A degree of freedom is thereby omitted in the method described above, which degree of freedom could, however, be permutatively compensated.

In the method described in the preceding, the form of the magnetic fields generated by the magnetic field coil and the gradient field has been assumed as given, and these field imperfections have been brought to a destructive superposition at a desired location to calculate an optimal gradient strength. Alternatively, the possibility exists to modify the shape of the gradient coil in hardware such that the nonlinearity of the gradient field optimally counteracts the inhomogeneities of the basic magnetic field. Accordingly, the $B_0$ field inhomogeneities can also be adjusted via adaptation of the magnetic field coil or, respectively, the shim plates to the nonlinearities of the gradient field.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to image a partial region of an examination subject in an Imaging system across at least two measurement slices, comprising:
    positioning an examination subject in a magnetic resonance data acquisition unit, having a field of view, with a partial region of the examination subject, of which a magnetic resonance image is to be obtained, being located at least in part at an edge of said field of view, said data acquisition unit comprising a gradient coil system and a basic field magnet;
    with a computer system, operating said magnetic resonance data acquisition unit with a data acquisition pulse sequence in order to acquire magnetic resonance data of said partial region in a multi-slice measurement in which a slice selection gradient and a readout gradient are activated by the gradient coil system of the data acquisition unit, that respectively produce a slice selection gradient field and a readout gradient field while a basic magnetic field is generated by the basic field magnet of the magnetic resonance data acquisition unit;
    operating said magnetic resonance data acquisition unit with said pulse sequence in order to optimize each voxel in said image, that is located at said edge of said field of view, in each of said measurement slices of said partial region, by configuring at least one of said slice selection gradient, or said readout gradient of said pulse sequence, as an at least one configured gradient in said pulse sequence, in order to make a distortion caused by a non-linearity of the respective gradient field of said at least one configured gradient, cancel a distortion caused by a basic magnetic field inhomogeneity of said basic magnetic field that exists at each of said voxels being optimized at said edge of said field of view; and
    with said computer system, reconstructing an image of said partial region from said acquired magnetic resonance data.

2. A method as claimed in claim 1 comprising configuring each configured gradient, of said pulse sequence, by:
    determining, with said computer system, a relative gradient field error at the respective voxel at the edge of the field of view;
    determining, with said computer system, said basic magnetic field inhomogeneity at the respective voxel at the edge of the field of view; and also
    determining, with said computer system, the configured gradient as a result of the determined relative gradient field error and the determined basic magnetic field inhomogeneity at the respective voxel.

3. A method as claimed in claim 2 comprising configuring each gradient field G of each configured gradient field, in the pulse sequence with said computer system according to:

$$G = -dB_0(\Delta x, \Delta y, \Delta z)/c(\Delta x, \Delta y, \Delta z)$$

wherein $dB_0$ is the basic magnetic field inhomogeneity at the respective voxel $(\Delta x, \Delta y, \Delta z)$ at said edge of said field of view; and
wherein c is the relative gradient field error at the respective voxel $\Delta x, \Delta y, \Delta z)$ at the edge of the field of view.

4. A method as claimed in claim 1 comprising selecting said partial region of said examination subject in order to comprise an anatomical structure of a patient that is located at said edge of said field of view of said magnetic resonance data acquisition unit.

5. A method as claimed in claim 4 comprising selecting said partial region in order to encompass an arm of a human as said examination subject.

6. A method as claimed in claim 1 wherein said magnetic resonance data acquisition unit comprises a tunnel-shaped opening in which said examination subject is located, and wherein said edge of said field of view comprises a sleeve proceeding along an inner surface of said tunnel-shaped opening.

7. A method as claimed in claim 6 wherein said sleeve has a sleeve thickness of 5 cm.

8. A method as claimed in claim 1 comprising operating said magnetic resonance data acquisition unit in order to acquire said magnetic resonance data in a transverse plane with respect to the examination subject.

9. A method as claimed in claim 1, wherein said imaging system further comprises a positron emission tomography data acquisition unit, and comprising, in said computer system, determining an attenuation correction when acquiring positron emission tomography data, dependent on said reconstructed image of said partial region.

10. An imaging apparatus comprising:
    a magnetic resonance data acquisition unit having a field of view, a gradient coil system, and a basic field magnet that generates a basic magnetic field;
    said magnetic resonance data acquisition unit having a patient opening therein that is configured to receive an examination subject in the magnetic resonance data acquisition unit, with a partial region of the examination subject, of which a magnetic resonance image is to be obtained, being located at least in part at an edge of said field of view;
    a processor configured to operate said magnetic resonance data acquisition unit with a data acquisition pulse sequence in order to acquire magnetic resonance data of said partial region in a multi-slice measurement in which a slice selection gradient and a readout gradient are activated in order to cause the gradient coil system of the magnetic resonance data acquisition unit to produce a slice selection gradient field and a readout gradient field, while the basic magnetic field is generated by the basic field magnet of the magnetic resonance data acquisition unit;
    said processor being configured to operate said magnetic resonance data acquisition unit with said pulse sequence in order to optimize each voxel in said image, that is located at said edge of said field of view, in each of said measurement slices of said partial region, by configuring at least one of said slice selection gradient, or said readout gradient within said pulse sequence, as an at least one configured gradient in said pulse sequence, in order to make a distortion caused by a non-linearity of the respective gradient field of said at least one configured gradient, cancel a distortion caused by a basic magnetic field inhomogeneity of said basic magnetic field that exists at each of said voxels being optimized at said edge of said field of view; and an image computer configured to reconstruct a magnetic resonance image of said partial region from said acquired magnetic resonance data.

11. An imaging apparatus as claimed in claim 10 further comprising a positron emission tomography data acquisition unit, and wherein said processor is also configured to determine positron emission tomography data acquisition unit parameters that operate said positron emission tomography data acquisition unit, dependent on said reconstructed magnetic resonance image of said partial region.

12. A non-transitory, computer-readable data storage medium encoded with programming instructions, said data storage medium being loaded into a computerized control and evaluation unit of an imaging apparatus said imaging apparatus comprising:

a magnetic resonance data acquisition unit having a field of view;

a gradient coil system that generates respective gradient fields, each exhibiting a gradient;

a basic field magnet that generates a basic magnetic field; and an opening configured to receive an examination subject in the magnetic resonance data acquisition unit with a partial region of the examination subject, of which a magnetic resonance image is to be obtained, being located at least in part at an edge of said field of view;

said programming instructions causing said control and evaluation system to:

operate said magnetic resonance data acquisition unit with a data acquisition pulse sequence in order to acquire magnetic resonance data of said partial region in a multi-slice measurement in order to cause a slice selection gradient and a readout gradient to be activated by the gradient coil system of the data acquisition unit that respectively produce a slice selection gradient field and a readout gradient field, while the basic magnetic field is generated by the basic field magnet of the magnetic resonance data acquisition unit;

operate said magnetic resonance data acquisition unit with said pulse sequence in order to optimize each voxel in said image, that is located at said edge of said field of view, by configuring at least one of said slice selection gradient, or said readout gradient within said pulse sequence, as an at least one configured gradient in said pulse sequence, in order to make a distortion caused by a non-linearity of the respective gradient field of said at least one configured gradient, cancel a distortion caused by a basic magnetic field inhomogeneity of a basic magnetic field that exists at each of said voxels being optimized at said edge of said field of view; and reconstruct a magnetic resonance image of said partial region from said acquired magnetic resonance data.

13. A non-transitory, computer-readable data storage medium as claimed in claim 12 wherein said programming instructions cause said control and evaluation system to determine positron emission tomography data acquisition parameters dependent on said reconstructed magnetic resonance image of said partial region, and subsequently operate a positron emission tomography data acquisition unit of the imaging apparatus with said position data acquisition parameters in order to acquire positron emission tomography data from said partial region.

* * * * *